(12) United States Patent
Organ et al.

(10) Patent No.: US 11,903,632 B2
(45) Date of Patent: Feb. 20, 2024

(54) METHOD AND APPARATUS FOR PRECISELY CONTROLLING THE SIZE AND SHAPE OF RADIOFREQUENCY ABLATIONS

(71) Applicant: Diros Technology Inc., Markham (CA)

(72) Inventors: Leslie William Organ, Charleston, SC (US); Peter George Darmos, Willowdale (CA); Moshe Morrie Altmejd, Austin, TX (US); George Peter Darmos, Willowdale (CA); Ilya Gavrilov, Mississauga (CA); Joel Ironstone, Toronto (CA)

(73) Assignee: DIROS TECHNOLOGY INC., Markham (CA)

( * ) Notice: Subject to any disclaimer, the term of this patent is extended or adjusted under 35 U.S.C. 154(b) by 0 days.

(21) Appl. No.: 13/652,455

(22) Filed: Oct. 15, 2012

(65) Prior Publication Data

US 2013/0096549 A1    Apr. 18, 2013

Related U.S. Application Data

(60) Provisional application No. 61/547,713, filed on Oct. 15, 2011.

(51) Int. Cl.
*A61B 18/14* (2006.01)
*A61B 18/12* (2006.01)
*A61B 18/00* (2006.01)

(52) U.S. Cl.
CPC .......... *A61B 18/14* (2013.01); *A61B 18/1206* (2013.01); *A61B 18/1477* (2013.01); *A61B 18/1492* (2013.01); *A61B 2018/0016* (2013.01); *A61B 2018/0072* (2013.01); *A61B 2018/00214* (2013.01); *A61B 2018/00577* (2013.01); *A61B 2018/00589* (2013.01); *A61B 2018/00654* (2013.01); *A61B 2018/00797* (2013.01); *A61B 2018/00821* (2013.01); *A61B 2018/124* (2013.01); *A61B 2018/126* (2013.01)

(58) Field of Classification Search
CPC .. A61B 2018/00577; A61B 2018/1467; A61B 2018/124; A61B 2018/126; A61B 18/14
USPC .......................................................... 606/34
See application file for complete search history.

(56) References Cited

U.S. PATENT DOCUMENTS

| | | | |
|---|---|---|---|
| 5,542,916 A | | 8/1996 | Hirsch et al. |
| 5,575,810 A | * | 11/1996 | Swanson et al. ............... 607/99 |
| 5,620,481 A | | 4/1997 | Desai et al. |
| 5,868,740 A | | 2/1999 | LeVeen et al. |
| 6,059,778 A | * | 5/2000 | Sherman ......................... 606/34 |
| 6,071,274 A | * | 6/2000 | Thompson et al. .......... 604/528 |
| 6,071,281 A | * | 6/2000 | Burnside et al. ............... 606/41 |
| 6,090,105 A | | 7/2000 | Zepeda et al. |
| 6,212,426 B1 | * | 4/2001 | Swanson ...................... 600/510 |

(Continued)

*Primary Examiner* — Michael F Peffley
*Assistant Examiner* — Yasamin Ekrami
(74) *Attorney, Agent, or Firm* — EVERMAN LAW FIRM, P.A.; Gregory R. Everman

(57) ABSTRACT

Various embodiments of multielectrode radiofrequency (RF) ablation probes are described herein that disclose methods and apparatus for improved control and predictability of the size and shape of RF thermal electrocoagulations. The features of the invention include the ability to make irregularly shaped ablations in order to conform to irregularly shaped target tissue volumes, and to make very large ablations without the requirement for electrode cooling.

15 Claims, 11 Drawing Sheets

(56) References Cited

U.S. PATENT DOCUMENTS

| Patent/Publication | Date | Inventor(s) | Class |
|---|---|---|---|
| 6,235,023 B1 | 5/2001 | Lee et al. | |
| 6,238,393 B1 | 5/2001 | Mulier et al. | |
| 6,632,221 B1 | 10/2003 | Edwards et al. | |
| 6,635,056 B2* | 10/2003 | Kadhiresan et al. | 606/34 |
| 6,652,516 B1 | 11/2003 | Gough | |
| 6,911,019 B2 | 6/2005 | Mulier et al. | |
| 7,367,974 B2* | 5/2008 | Haemmerich et al. | 606/41 |
| 7,722,606 B2 | 5/2010 | Azure | |
| 7,794,458 B2 | 9/2010 | McIntyre et al. | |
| 8,142,428 B2 | 3/2012 | Ostrovsky et al. | |
| 8,221,406 B2* | 7/2012 | Desinger et al. | 606/34 |
| 2002/0022864 A1* | 2/2002 | Mahvi | A61B 18/1477 607/2 |
| 2002/0111615 A1* | 8/2002 | Cosman et al. | 606/41 |
| 2002/0120260 A1 | 8/2002 | Morris et al. | |
| 2002/0161361 A1* | 10/2002 | Sherman et al. | 606/34 |
| 2003/0045871 A1 | 3/2003 | Jain et al. | |
| 2003/0069573 A1* | 4/2003 | Kadhiresan | A61B 18/1492 606/41 |
| 2003/0199862 A1* | 10/2003 | Simpson et al. | 606/34 |
| 2005/0080409 A1* | 4/2005 | Young | A61B 18/1482 606/41 |
| 2005/0107781 A1* | 5/2005 | Ostrovsky et al. | 606/41 |
| 2005/0288663 A1 | 12/2005 | Behzadian | |
| 2006/0015095 A1* | 1/2006 | Desinger et al. | 606/41 |
| 2006/0074413 A1* | 4/2006 | Behzadian | A61B 18/1477 606/41 |
| 2007/0055225 A1* | 3/2007 | Dodd et al. | 606/34 |
| 2007/0125662 A1* | 6/2007 | Dumont | A61B 18/1477 435/173.1 |
| 2008/0009847 A1 | 1/2008 | Ricart et al. | |
| 2008/0172048 A1* | 7/2008 | Martin | A61B 18/1442 606/10 |
| 2008/0243214 A1* | 10/2008 | Koblish | 607/115 |
| 2009/0076498 A1* | 3/2009 | Saadat | A61B 18/1492 606/41 |
| 2012/0089123 A1 | 4/2012 | Organ et al. | |
| 2017/0049513 A1* | 2/2017 | Cosman, Jr. | A61B 18/18 |

* cited by examiner

METHOD AND APPARATUS FOR PRECISELY CONTROLLING THE SIZE AND SHAPE OF RADIOFREQUENCY ABLATIONS

CROSS REFERENCE TO RELATED APPLICATIONS

This application claims the benefit of U.S. Provisional Application No. 61/547,713, filed Oct. 15, 2011, which is incorporated herein by reference.

BACKGROUND OF THE INVENTION

1. Field of the Invention

The present invention relates to the field of multielectrode radiofrequency ablation probes for therapeutic purposes and, more specifically, to multielectrode radiofrequency ablation probes and methods of use thereof for controlling the size and shape of radiofrequency ablations.

2. Description of the Related Art

The insertion of an insulated probe with one or more electrodes in its distal portion that is guided by X-ray or ultrasound imaging from the skin surface to a target tissue for the purpose of making either an electrocoagulative ablation or otherwise disabling cellular function is becoming increasingly common for applications such as the modification or destruction of neurogenic foci for the relief of intractable pain, or to eradicate diseases such as localized cancers. The energy for such minimally invasive, percutaneous techniques is frequently a radiofrequency (RF) generator, with the RF current entering the tissue at one or several uninsulated electrodes at or near a probe tip in a single probe or distributed in an array of separate probes. RF current produces tissue destruction by causing rapid oscillation of ions in the region of the probe tip. This results in frictional heating which, when it reaches about 47° C. and above, causes electrocoagulation, i.e. tissue destruction or ablation.

Tissue regions or structures intended for RF ablation may be irregularly shaped or extend non-uniformly. This often requires movement of the RF probe into different parts of a target region with repeated ablations at each new position to expand overall lesion size and shape. But these maneuvers can result in unpredictable lesions which are either too small or larger than required, leading to unnecessary tissue destruction or harming adjacent critical structures.

Attempts to generate large lesions, aside from simply increasing electrode size and number, include the use of tip cooling with internal circulating fluids to alter and extend the tissue heat pattern surrounding the tip, or designs where electrodes, retracted within a probe shaft, are extruded into the tissue at the open end of the probe tip or through slots in the probe shaft once the probe tip is at its target position. The electrodes can be straight or sprung steel or a memory metal such as nitinol so that when extruded assume a curved shape. Various configurations such as parallel electrodes, loops, and baskets result. But the target volume can still exceed the generated lesion volume, requiring probe repositioning and repeated RF ablations. In addition, ablation volume can be less than anticipated due to imperfections in the lesion making process or other limitations as the art is currently performed.

The present invention describes methods and versions of an apparatus that provide solutions to the above problems. A preferred embodiment of this invention is the unique manner in which a lesion is made to evolve. Another embodiment describes a method of precisely and independently controlling the temperature at each electrode in a multielectrode configuration, a technique particularly useful for the creation of large ablations and for matching ablations to irregularly shaped target areas. In addition, two versions of an apparatus for implementing the teachings of the invention are disclosed; one an RF generator based on multiple independent RF switch control, and the other an RF generator based on signal phase and amplitude control.

BRIEF SUMMARY OF THE INVENTION

To achieve the foregoing and other objects, the present invention, as embodied and broadly described herein, provides various embodiments of a multielectrode radiofrequency ablation probe and/or a plurality of radiofrequency ablation probes having one or more electrodes, and methods of use thereof for controlling the size and shape of radiofrequency ablations.

In accordance with an embodiment of the invention, a method is provided for forming an ablation. The method includes the steps of: providing a first bipolar electrode set having first and second electrode groups, the first electrode group including one or more electrodes and the second electrode group including one or more electrodes; providing a second bipolar electrode set having first and second electrode groups, the first electrode group including one or more electrodes and the second electrode group including one or more electrodes; applying energy for a period of time to the first electrode set capable of forming a portion of the ablation; next applying energy for a period of time to the second electrode set capable of forming a portion of the ablation; and repeating the steps of applying energy to the first and second electrode sets.

The method may also include: i) wherein the period of time for applying energy to the first electrode set is in the range of 10 milliseconds to 1500 milliseconds and wherein the period of time for applying energy to the second electrode set is in the range of 10 milliseconds to 1500 milliseconds; ii) wherein the frequency of repeating the steps of applying energy to the first and second electrodes sets is in the range of one per second to 25 per second, iii) wherein the number of times of repeating the steps of applying energy to the first and second electrode sets is at least 100 times, iv) wherein the first and second electrode sets share at least one electrode, v) wherein the first and second electrode set share a group of electrodes, vi) wherein the one or more electrodes of the second electrode group of the first set of electrodes is a plurality of electrodes; vii) the step of providing at least a third electrode set having first and second electrode groups, the first electrode group including one or more electrodes and the second electrode group including one or more electrodes, and using said first, second and third electrode sets in various combinations to create a three-dimensional, long, linear ablation volume and/or a three-dimensional non-linear ablation volume in order to conform in size and shape to a target volume; and/or viii) the step of causing tissue ablation by thermal electrocoagulation during the steps of applying energy to the first electrode set and applying energy to the second electrode set.

In accordance with another embodiment of the invention, a method is provided for forming an ablation by including the steps of providing a first electrode set having first and second electrode groups, the first electrode group, including one or more electrodes and the second electrode group including one or more electrodes; applying energy for a period of time to the first electrode set capable of forming a portion of the ablation; and repeating the step of applying energy to the first electrode sets.

The method may also include: i) wherein the second electrode group set creates a reference electrode which, although not necessarily symmetric relative to the first electrode group, has a virtual position that can be predicted by their configuration relative to the first electrode group, ii) wherein the second electrode group creates a virtual return path electrode whose position relative to the first electrode group can be predicted so that RF current can be directed from reaching areas where critical structures may be adversely affected, iii) wherein the first electrode group is one electrode and precise and independent control of the temperature of the one electrode of the first electrode group is made possible by combining two or more electrodes of the second electrode group into a return path electrode group so that current density at each of the electrodes in the return path is small relative to the current density at the one electrode, so that when a temperature change at the one electrode of the first electrode group is required, the modification of RF current to it will minimally affect the low impedance return path electrode group because the change in current will be distributed over the return path electrode group, iv) wherein the period of time for applying energy to an electrode set is sufficiently short so that only a small, incremental tissue ablation is made, v) wherein the period of time for applying energy to the first and/or second electrode sets is in the range of 10 milliseconds to 1500 milliseconds, vi) wherein the number of times of repeating the step of applying energy to the first electrode set is at least 100 times, and/or vii) the step of providing a second electrode set having first and second electrode groups, the first electrode group including one or more electrodes and the second electrode group including one or more electrodes, applying energy to the second electrode set capable of forming a portion of the ablations, and wherein the time between the step of repeated applications of energy to the first and second electrode sets is sufficiently short, in the range of 10 milliseconds to 330 milliseconds, so that heat generated from the previous application does not decrease appreciably.

In accordance with another embodiment of the invention, a method is provided for providing a first electrode set having first and second electrode groups, the first electrode group including one or more electrodes and the second electrode group including one or more electrodes; providing a second electrode set having first and second electrode groups, the first electrode group including one or more electrodes and the second electrode group including one or more electrodes; applying energy for a brief period of time to the first electrode set capable of forming a small, incremental portion of a target ablation volume; and applying energy for a brief, generally equal portion of time to the second electrode set capable of forming a small, incremental portion of the target ablation volume; and repeating the steps of similarly applying energy to the first and second electrode sets so that ablation volume increases in at least 100 incremental steps in a controlled, predictable manner until the target ablation volume is reached.

The method may also include: i) wherein by the disposition of the first and second electrode groups of unequal lengths and/or in various directions at a distal end portion of at least one probe of the first electrode set, an irregular ablation volume can be created that generally matches the size and shape of the target ablation volume, ii) wherein by the disposition of first and second electrode groups of unequal lengths and/or in various directions at a distal end portion of at least one probe of the first electrode set, an ablation volume can be created that is offset from the probe central longitudinal axis in order to be directed towards the target ablation volume, iii) wherein by the disposition of first and second electrode groups of unequal lengths and/or in various directions at a distal end portion of at least one probe of the first electrode set, an ablation volume can be created that is offset from the probe central longitudinal axis in order to be directed towards the target ablation volume and away from adjacent structures that would be adversely affected if exposed to the ablation process, iv) wherein the second electrode group of the first electrode set creates a reference electrode which, although not necessarily symmetric relative to the first electrode group of the first electrode set, has a virtual position that can be predicted by their configuration relative to the first electrode group of the first electrode set, v) wherein the second electrode group creates a virtual return path electrode whose position relative to the first electrode group of the first electrode set can be predicted, and thereby allow 3-dimensional lesion volume to be created in a predictable manner, vi) wherein the virtual return path electrode is used to direct the flow of RF current so that RF current can be prevented from reaching areas where critical structures may be adversely affected, and/or vii) wherein the first electrode group of the first electrode group is one electrode and precise and independent control of the temperature of the one electrode of the first electrode group is made possible by combining two or more electrodes of the second electrode group into a return path electrode group so that current density at each of the electrodes in the return path is small relative to the current density at the one electrode of the first electrode group, so that when a temperature change at the one electrode of the first electrode group is required, the modification of RF current to it will minimally affect the low impedance return path electrode group because the change in current will be distributed over the return path electrode group.

In accordance with an embodiment of the invention, an RF generator is provided having a multiple independent radiofrequency (RF) switch control, wherein a network topology of in general a number N of RF switch connections, SW1 to SWN, to a target at N target nodes with RF current flowing in predetermined pattern, can be repeated and/or reconfigured within a cycle and subsequent cycles by operably maintaining or changing connections to one or more electrodes of an electrode group having at least one electrode to respond to temperature and heating requirements of any of the one or more electrodes at any instant; and wherein changing connections causes RF current to flow in another predetermined pattern. Preferably, the connection to an electrode or group of electrodes can be intelligently switched by software means between three states: current Injection, current return, and disconnection.

In accordance with another embodiment of the invention, an RF generator is provided having a signal phase and amplitude control wherein a network topology of in general a number N of proportional RF adders connected to N target nodes can provide essentially an infinite number of RF phase and amplitude combinations to the N target node connections; wherein the combinations can be repeatedly changed within the lesion cycle to respond to the temperature and heating requirements at an electrode and/or electrode group any instant; and form other geometric configurations of electrodes or electrode groups. Preferably, the connection to the electrode and/or group of electrodes can be intelligently switched by software means between three states: current Injection, current return, and disconnection, and all changes in signal phase and amplitude are obtained without the need to disconnect any of the electrode connections.

In accordance with an embodiment of the present invention, a method for forming an ablation includes the steps of providing a first bipolar electrode set having first and second electrode groups, the first electrode group including one or more electrodes and the second group including one or more electrodes; providing a second bipolar electrode set having first and second electrode groups, the first electrode group including one or more electrodes and the second group including one or more electrodes; applying energy for a period of time to the first bipolar electrode set capable of forming a first portion of the ablation; applying energy for a period of time to the second bipolar electrode set capable of forming a second portion of the ablation; and repeating the steps of applying energy to the first and second bipolar electrode sets. Preferably, the period of time for applying energy to the first bipolar electrode set is in the range of 50 milliseconds to 500 milliseconds, in the range of 50 milliseconds to 500 milliseconds for the second bipolar electrode set, wherein the cycle of application of RF energy to all bipolar electrode sets is preferably repeated at a frequency of once per second to 10 times per second, and the total number of cycles is at least 100. Consequently, RF ablation volume is not generated entirely at a first bipolar electrode set, and then at a second bipolar electrode set; rather there is a process wherein there is a gradual, incremental, and concurrent development of ablation volume at all bipolar electrode sets.

In accordance with another embodiment of the present invention, a method for forming an ablation includes providing a first electrode set having first and second electrode groups, the first electrode group including one or more electrodes and the second electrode group including one or more electrodes; applying energy for a period of time to the first electrode set capable of forming a first portion of the ablation; and repeating the step of applying energy to the first electrode set. Preferably, the period of time for applying energy to the first electrode set is in the range of 50 milliseconds to 500 milliseconds, and the application of RF energy to the first electrode set is preferably repeated at a frequency of once per second to 10 times per second, and the total number of repetitions is at least 100.

BRIEF DESCRIPTION OF THE DRAWINGS

The above described and other features, aspects, and advantages of the present invention are better understood when the following detailed description of the invention is read with reference to the accompanying drawings, wherein.

DESCRIPTION OF THE PREFERRED EMBODIMENTS

The present invention will now be described more fully hereinafter with reference to the accompanying drawings in which preferred embodiments of the invention are shown. This invention may, however, be embodied in many different forms and should not be considered as limited to the embodiments set forth herein. These exemplary embodiments are provided so that this disclosure will be both thorough and complete, and will fully convey the scope of the invention to those skilled in the art.

Figure 1A:
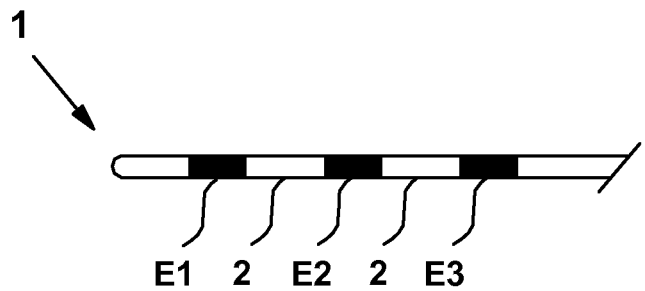
FIGS. 1A to 1D show the assumed shape of two bipolar RF electrocoagulations made in a conventional manner in a three electrode RF probe.
Figure 1B:
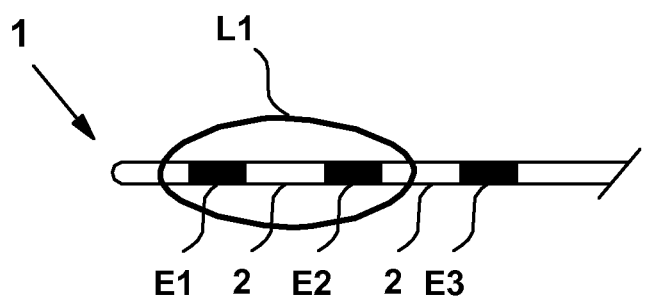
Figure 1C:
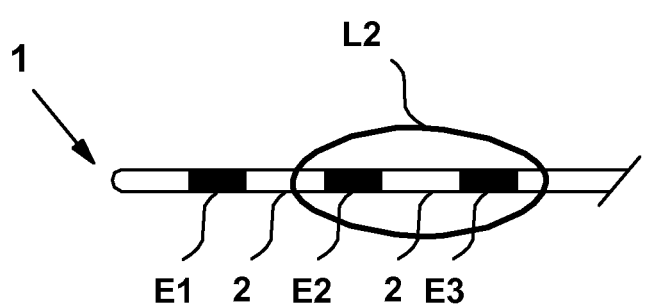
Figure 1D:
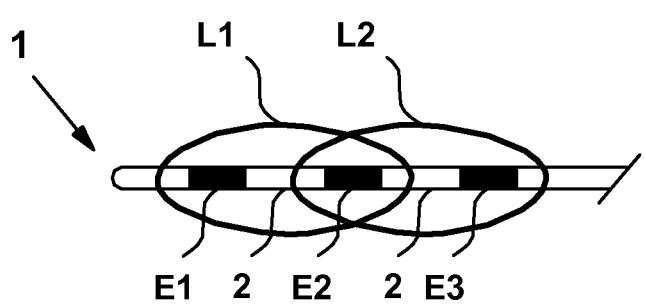

Controlling Multielectrode RF Ablation Development by Incremental and Sequentially Distributed RF Applications A method of augmenting radiofrequency (RF) lesion size is to make a series of bipolar RF ablations using different combinations of electrodes in multielectrode probes. A prior art process is illustrated in FIGS. 1A to 1D which shows three electrodes, E1, E2, and E3 at the distal end portion of a multielectrode RF ablation probe 1. The electrodes are separated by probe insulation 2. Radiofrequency generators typically have two active terminals (outputs), one that delivers an RF voltage into a target tissue, and the other that serves as a return path for the resultant RF current. FIG. 1A shows the distal end portion of multielectrode RF ablation probe 1 with three electrodes E1, E2, and E3. FIG. 1B shows a first RF ablation with the RF generator voltage output and return path input directed to electrodes E1 and E2, resulting in the formation of an elliptical electrocoagulation L1. In the next step, FIG. 1C, RF generator activation is directed to electrodes E2 and E3 for a second RF ablation forming, it is generally assumed, the elliptical electrocoagulation L2. In theory, the overall outcome, shown in FIG. 1D, is essentially identical electrocoagulations L1 and L2 with some overlap, thus providing an elongated lesion.

Figure 2A:
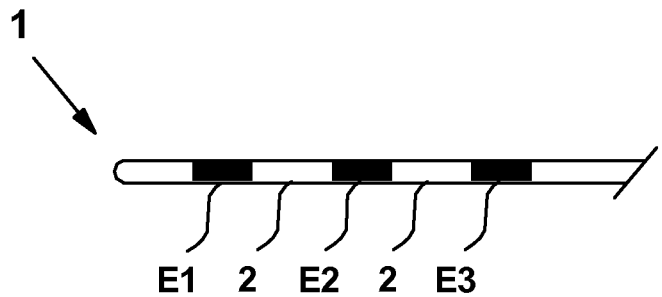
FIGS. 2A to 2D illustrate the disparity in the resistance of electrode tissue interfaces when RF electrocoagulations are made in a conventional manner, and the effect on lesion volume in practice.
Figure 2B:
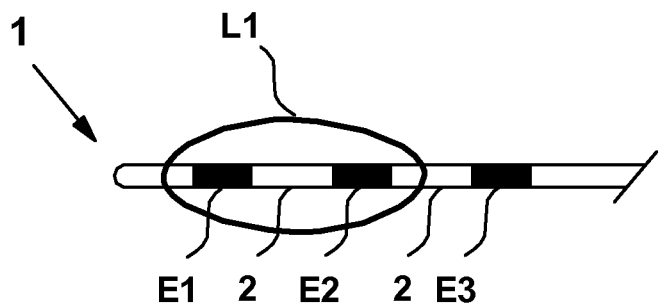
Figure 2C:
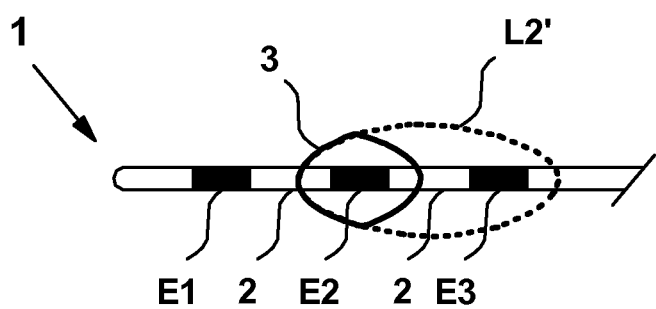
Figure 2D:
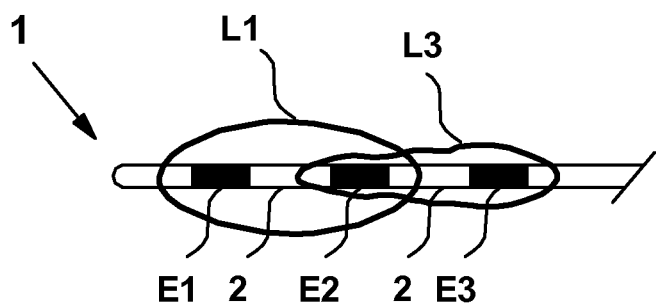

FIGS. 2A to 2D again show the distal end portion of RF ablation probe 1 with electrodes E1, E2, and E3, and probe insulation 2 being used in accordance with a prior art process. FIG. 2B again shows a first RF ablation with the RF generator output directed to electrodes E1 and E2, resulting in the formation of an elliptical electrocoagulation L1. In FIG. 2C, where the RF generator output is directed to electrodes E2 and E3, the conventionally expected second electrocoagulation L2' is shown in dotted outline. But the initial condition of electrode E2 is changed: a part of electrocoagulation L1 covers and partially insulates electrode E2, i.e. a volume 3 which is formed by the overlap of electrocoagulation L1. Because of the higher resistance surrounding electrode E2, in practice the second electrocoagulation L3 in FIG. 2D will be smaller than electrocoagulation L2 of FIG. 1 and as well will be irregularly shaped.

A preferred embodiment of this invention avoids the above described disparity of resistance at electrode tissue interfaces. It does so by a gradual, incremental, and concurrent development of ablation volume at all bipolar electrode sets instead of, as in current practice, first making a completed ablation at one bipolar electrode set before proceeding to the next bipolar set. In the context of this invention, a bipolar electrode set includes two electrode groups simultaneously activated, with each group including one or more electrodes.

Figure 3A:
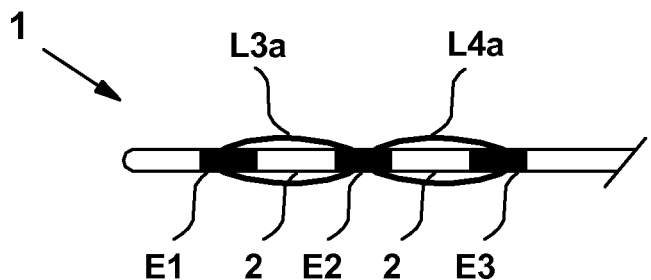
FIGS. 3A to 3C show a preferred embodiment of the invention, an RF electrocoagulation process applying incremental and sequentially distributed RF applications with a multielectrode RF ablation probe.
Figure 3B:
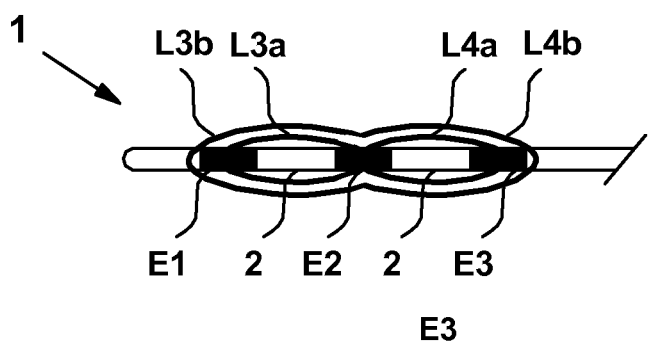
Figure 3C:
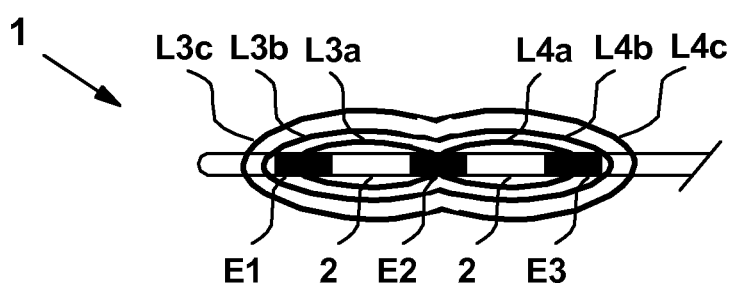

In the example of FIGS. 3A to 3C, the distal end portion of a conventional RF ablation probe 1 with electrodes E1, E2, and E3 and probe insulation 2 is shown; however, the formation of the RF ablations is in accordance with a preferred embodiment of the invented method. There is one electrode in each group, i.e. the bipolar electrode set consists of two electrodes. Under control of the RF generator to be described later, instead of continuously applying RF current to any one bipolar electrode set, for example for 90 seconds in order to make a complete ablation, RF current is sequentially applied to all bipolar electrode sets for a brief period of time, for example 100 milliseconds, and when completed the cycle is repeated, in this example about 900 times so that each electrode set receives in effect a 90 second application of lesion current. The repeated cycles of incremental and sequentially distributed RF applications is equivalent to a continuously applied RF application because the time constant of heat decay in tissue is very long compared to the repetition cycle of the RF current.

The process of sequentially distributed then repeated very short applications of RF current is illustrated in FIGS. 3A to 3C. FIG. 3A represents a time early in the process with a small number of cycles of RF current application to two bipolar electrode sets, electrode group E1 and E2 and electrode group E2 and E3. Relatively small but equal RF electrocoagulations L3a and L4a have been created at these electrode sets. FIG. 3B represents an intermediate point in the process, with the electrocoagulations reaching ablation volumes L3b and L4b. Ablation volumes L3a and L4a are now lightly stippled to indicate further development of the electrocoagulations in each of these volumes. FIG. 3C represents a later point in the process, with the electrocoagulations reaching ablation volumes L3c and L4c, with the ablation volumes L3a and L4a now darkly stippled and ablation volumes L3b and L4b lightly stippled to indicate the further development of the electrocoagulations in each of these volumes. Even though electrode tissue interface resistance increases, as it normally does during RF lesion development, it does so equally and in a controlled manner in this invention, resulting in equal and predictable RF electrocoagulations at all bipolar electrode sets. The application time of RF current to each bipolar electrode set during a cycle is preferably in the range of 50 milliseconds to 500 milliseconds, although application times beyond these limits may advantageously be used; e.g. 10 milliseconds to 1500 milliseconds. The rate at which the application to all bipolar electrode sets is repeated, i.e. the frequency, can preferably range from once per second to 10 per second, although values beyond these limits may advantageously be used; e.g. once per second to 25 per second. The total number of cycles is ideally at least 100. RF power output level depends primarily on electrode gauge and length and size of the target ablation volume. A typical range is 0.5 to 25 watts, but as little as 0.1 watt or up to 50 watts may be required.

A feature of this embodiment is the inclusion of temperature sensors such as thermocouples in the multielectrode probes within or close to some or all of the electrodes in order to provide information about tissue temperature adjacent to each electrode. Although constantan and copper are used here for the thermocouple junction, other metal pairs well known to the industry such as nickel-chromium and nickel can also be used. Temperature sensors allow feedback control in order to adjust RF current or application time to each bipolar electrode set if required. Similarly, tissue impedance, RF current and RF voltage can also be monitored to assess the development of the electrocoagulations at each bipolar electrode set, and adjustments made if indicated.

Although the use and advantages of incremental and sequentially distributed RF applications has been described with the example of multiple electrodes on a single probe, it applies equally to multiple electrodes on separate probes, or some combination thereof.

Figures 4A, 4B, 4C:
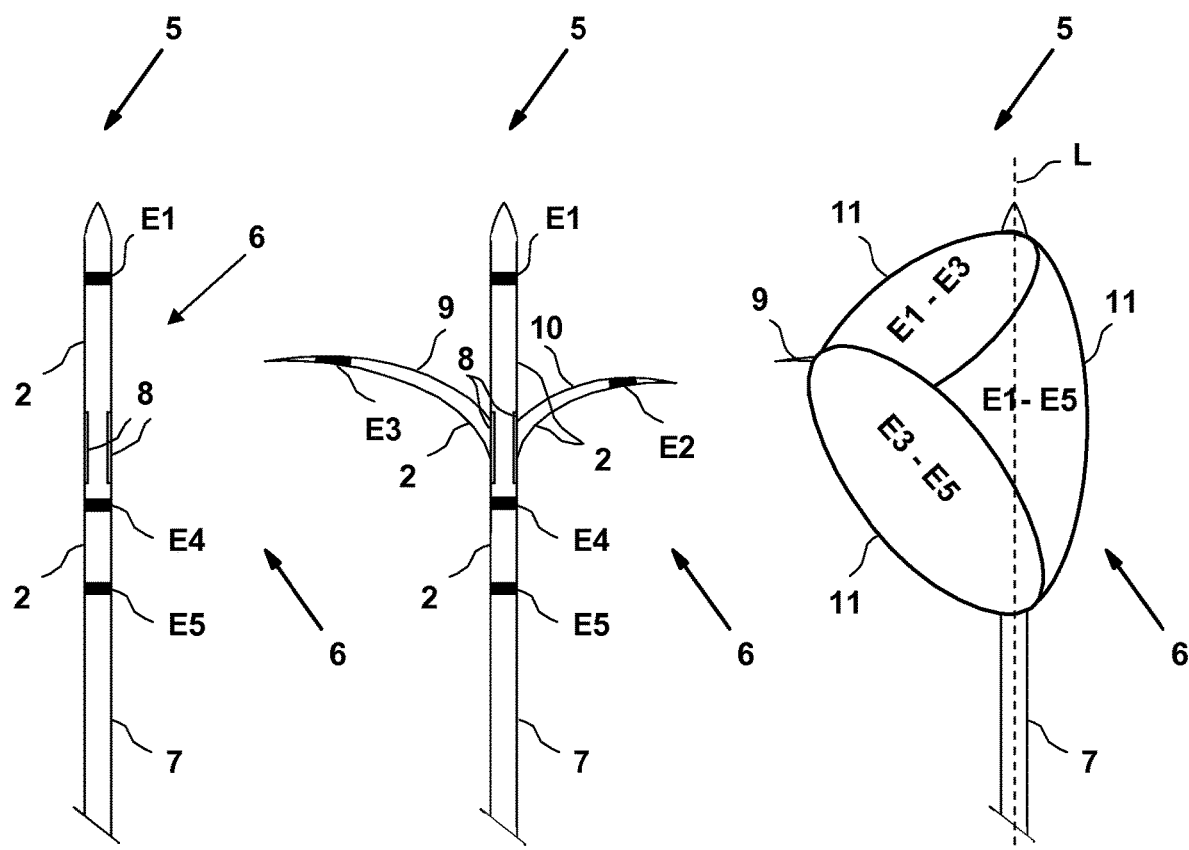
FIGS. 4A to 4C show another preferred embodiment of a multielectrode RF ablation probe with at least some electrodes that can be retracted within the lumen of the probe and then be variably deployed at a target site to allow creation of uniform or irregularly shaped RF ablations.

Matching RF Ablation Volume and Shape to Tissue Target Volume and Shape with Multielectrode RF Probes In another preferred embodiment an RF probe with a plurality of electrodes positioned within a target tissue region forms an electrode array. Some or all the electrodes can be variably deployed, for example, from a catheter lumen as shown in multielectrode RF ablation probe 5 of FIGS. 4A to 4C. Multielectrode RF probe 5 includes a distal end portion 6, a tubular probe body 7, only part of which is shown, and a proximal connector hub, not shown. The tubular probe body 7 and distal end portion 6 are constructed of surgical grade stainless steel, or other suitable electrically conducting material, and is insulated with a smooth polymer coating or other suitable insulating material with the electrodes being separated by insulation 2. The proximal connector hub is preferentially plastic, but it could be constructed of other suitable non-conductive material or insulated metal. The outer diameter of distal end portion 6 and tubular probe body 7 is typically about 18 gauge (1.27 mm), but other larger or smaller diameters such as 16 gauge (1.65 mm) or 20 gauge (0.90 mm) could be used according to the clinical application. FIG. 4A shows three ring-shaped conductive electrodes, E1, E4, and E5, on distal end portion 6. The length of these electrodes is typically 5 mm to 15 mm, but longer or shorter lengths could advantageously be used. A variety of multielectrode constructions have been described in U.S. patent application Ser. No. 13/188,101, filed Jul. 21, 2011, which this application incorporates by reference.

FIGS. 4A and 4B show two slots 8 on distal end portion 6 which, as shown in FIG. 4B, allow for the extrusion of pre-curved stainless steel tubes 9 and 10 which are insulated 2 except in the regions forming electrodes E2 and E3. Stainless steel tubes 9 and 10 can be equal in length or of different lengths, and can be tubular as described to allow the incorporation of a temperature sensor, or solid if no temperature monitoring is required. As with electrodes E1, E4, and E5, a range of electrode lengths or configurations could be used dependent upon the application. Stainless steel tubes 9 and 10 are retracted within distal end portion 6 during, for example, an image guided, percutaneous approach to the target site. When distal end portion 6 is in the desired position, stainless steel tubes 9 and 10 are advanced laterally out through slots 8 until electrodes E2 and E3 reach their target positions. A feature of this invention allows such stainless steel tubes to be extruded unequally, as with electrode E3 in FIG. 4B which has been extended further than electrode E2 to allow the creation of an irregularly shaped electrocoagulation to match a similarly irregularly shaped tissue target. Stainless steel tubes 9 and 10 can be tapered, or otherwise pointed, for ease of transit through tissue. Within some, or all, the lumens corresponding to the position of the five electrodes of the RF ablation probe are thermocouple heat sensors for monitoring lesion temperature.

FIG. 4C shows three bipolar RF ablations 11 between electrodes E1-E3, E1-E5, and E3-E5, selected to match an irregularly shaped tissue target which is offset from the probe's central longitudinal axis (L). Each bipolar RF ablation is applied briefly and in rapid succession, then in repeated cycles as described previously, creating the three confluent, ellipsoidal RF ablations 11. Furthermore, Electrodes E2 and E3 can be retracted to allow probe rotation, and then the electrodes advanced again to orientate a next lesion volume in another plane.

It can be appreciated that other configurations of multi-electrode RF probes can be constructed such as with fewer or more than five electrodes, variations in electrode size and shape, different degrees of extension of one or more electrodes from the probe, more slots on the probe distal end portion for electrode extrusion in different planes in order to increase 3-dimensional coverage, and the addition of one or a cluster of electrodes extending from the end of the RF probe. In addition, electrodes retracted within the probe can become curved when extended by using a memory metal such as Nitinol or sprung steel. Furthermore, the described multiple electrodes and their manner of deployment, and the configurations formed, can be attained by using two or more RF probes simultaneously, both multielectrode, or one with a single electrode, or both with single electrodes.

In general, and to add further flexibility, electrodes can be operated in monopolar mode wherein one or more electrodes receive the RF output voltage and one or more electrodes serve as a distant return path.

Figure 5A:
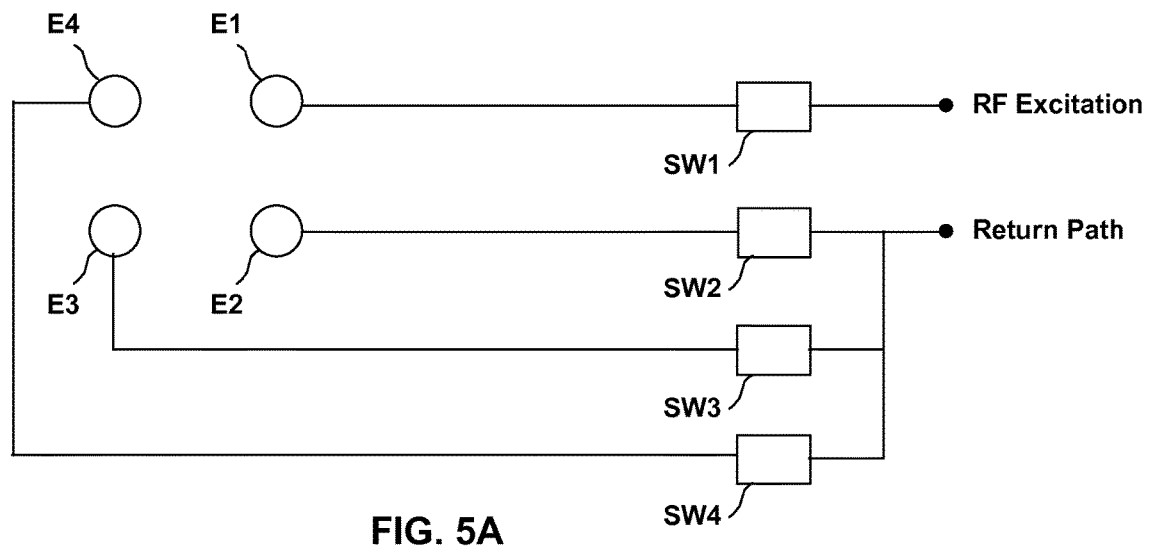
FIGS. 5A to 5E illustrate a method of precisely and independently controlling the temperature at each electrode receiving RF excitation voltage in multielectrode probes, and examples of RF ablations using this method.

Precise and Independent Control of the Temperature at Each Electrode in Multielectrode Configurations Another preferred embodiment of this invention provides precise and independent control of the temperature at each electrode receiving RF excitation voltage in multielectrode probes during the ablation process. FIG. 5A shows an array of four electrodes, E1, E2, E3, and E4, each connected to an RF generator switch, switches SW1, SW2, SW3, and SW4 respectively. The four electrodes may comprise a group extending from a single RF probe, or be an electrode tip on four RF probes. A first bipolar electrode set comprises electrode E1 which is connected to the RF excitation voltage, and an electrode group comprising electrodes E2, E3, and E4 that serve as a combined, low impedance return path electrode. Consequently, current density at each of these electrodes is small relative to the current density at electrode E1, allowing RF energy focus at electrode E1 so that when RF current is modified based on temperature feedback from electrode E1, the low impedance return path electrode group will be minimally affected, allowing temperature changes primarily at electrode E1 and the creation of a precisely controlled ablation L1, shown in FIG. 5B.

Figures 5B, 5C:
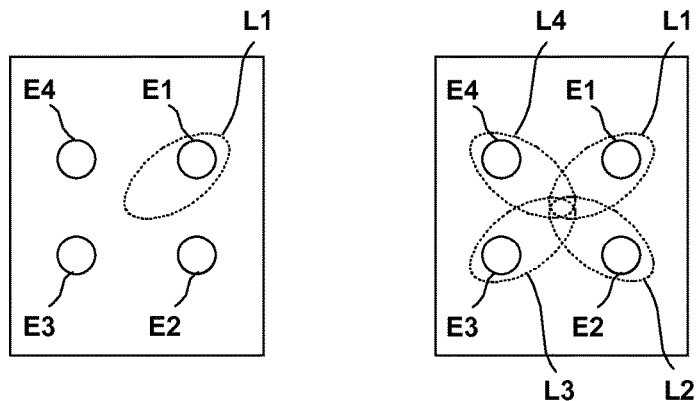

When this "one electrode vs. many" procedure is repeated for all electrodes, using the repetitive process of gradual, incremental, and concurrent ablation development of this invention, elliptical ablation volumes L1, L2, L3, and L4, arranged in a stellate configuration, are formed, as shown in FIG. 5C. If stop-motion observation of the creation of this RF ablation were possible over the hundred or more cycles of RF current application to the four bipolar electrode sets, a very slowly and symmetrically enlarging stellate-shaped lesion would be observed.

Figure 5D:
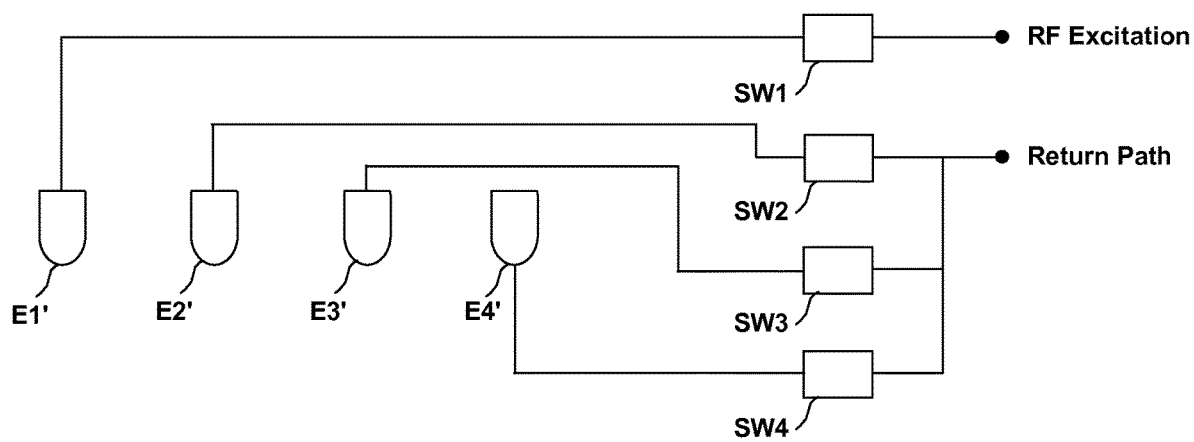
Figure 5E:
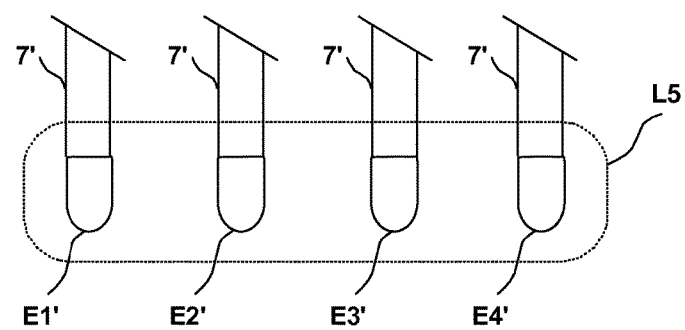

FIG. 5D shows the same connection of four electrodes, E1', E2', E3', and E4' to RF generator switches SW1, SW2, SW3, and SW4 as used in FIG. 5A, i.e. a first bipolar electrode set comprises electrode E1' which is connected to the RF excitation voltage, and an electrode group comprising electrodes E2', E3', and E4' that serve as a combined, low impedance return path. In FIG. 5D, E1', E2', E3', and E4' represent the electrode tips of four RF probes arranged in an equally spaced, parallel configuration as in, for example, on the dorsal aspect of the sacrum for RF denervation of sacral sensory nerves for treatment of chronic sacroiliac joint pain. FIG. 5E further illustrates probe arrangement by showing part of the tubular probe body 7'. Following the teaching of this invention, the "one electrode vs. many" lesion process of incremental and sequentially distributed applications of RF current is used as previously described wherein each electrode in turn is connected to the RF excitation voltage and the other three electrodes are joined together to serve as a combined, low impedance return current path. The result in shown in FIG. 5E, a continuous linear lesion L5 of a generally rectangular shape with rounded corners, enclosing the four electrodes.

Figure 6A:
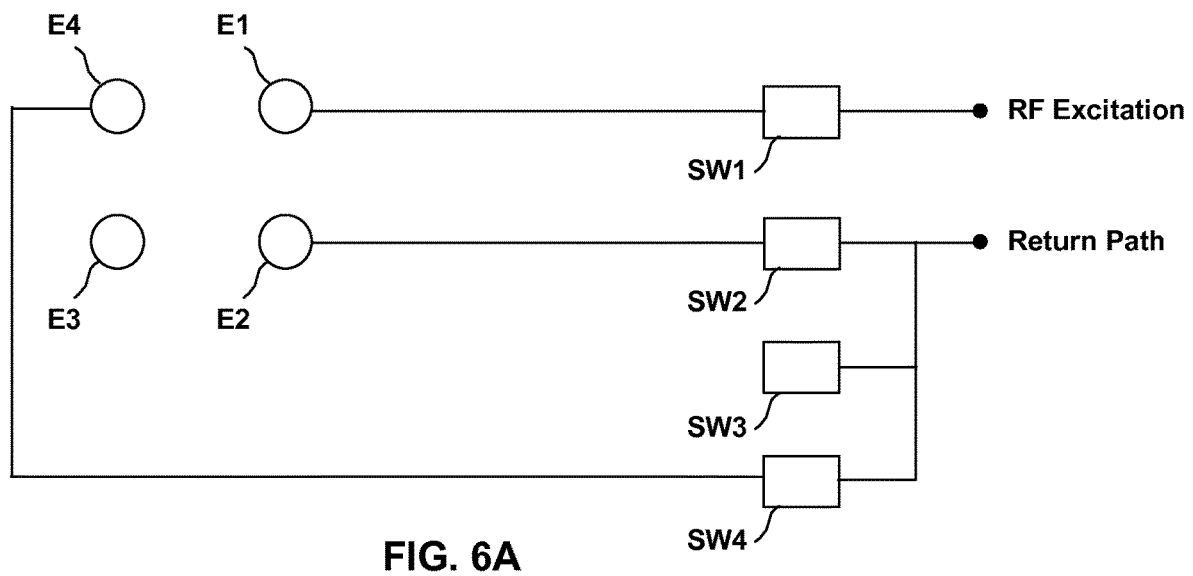
FIGS. 6A and 6B show the use of the method in FIG. 5A for another configuration of electrodes and the resultant shape of the RF ablation.
Figure 6B:
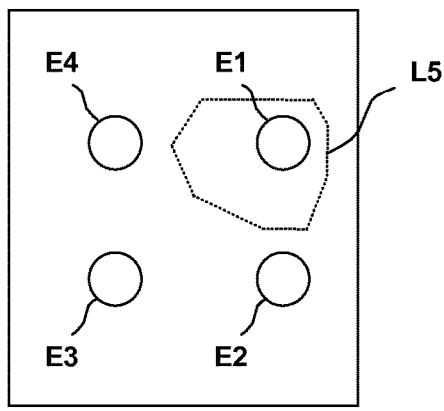

In another example electrode configuration, switch SW3 is open but switches SW2 and SW4 remain closed, leaving electrodes E2 and E4 for the return path, as shown in FIG. 6A, creating another lesion shape L5 shown in FIG. 6B as may be required for an application.

Figure 7A:
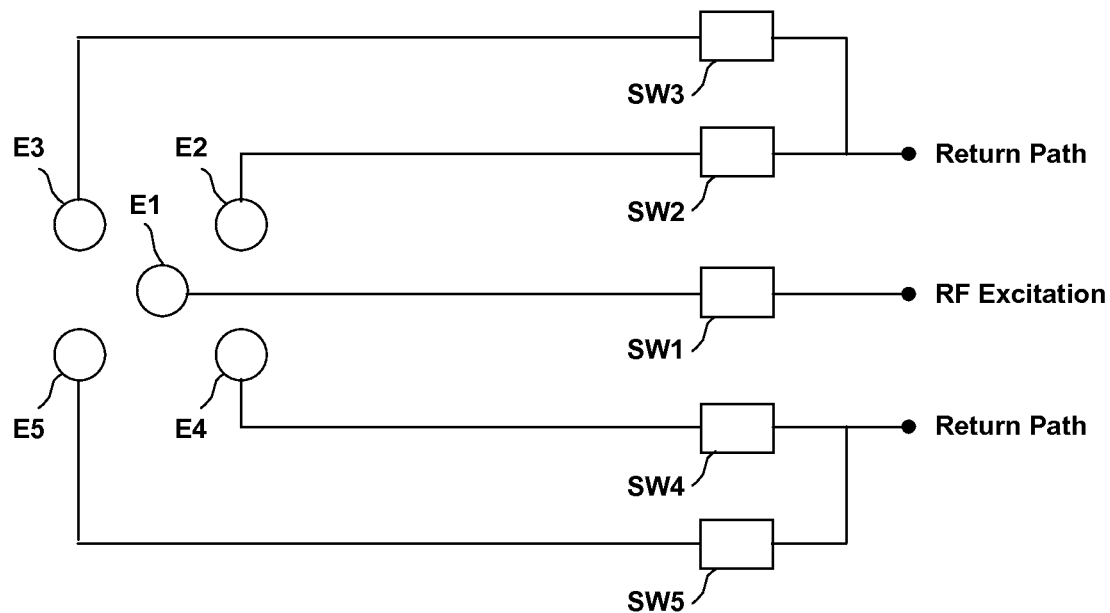
FIGS. 7A to 7D show the use of the method in FIG. 5A for yet another configuration of electrodes and the resultant shapes of the RF ablations.
Figure 7B:
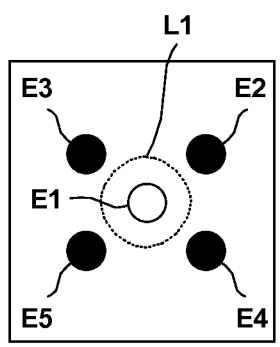

In yet another example electrode configuration, a plurality of electrodes includes two or more outer electrodes substantially defining an ablation volume and at least one centrally positioned electrode. FIG. 7A shows a configuration of five electrodes, a central electrode E1, and four outer, circumferential electrodes E2, E3, E4, and E5 which are connected to switches SW1, SW2, SW3, SW4 and SW5 respectively. In a first example, SW2, SW3, SW4 and SW5 are closed and are all connected to the return path of the RF generator, and SW1 is connected to the RF excitation voltage. This configuration establishes a virtual remote, symmetrical return path "electrode" that is not remote, but instead closely surrounds the active electrode E1 and therefore provides greater control of lesion shape and avoids the flow of RF current elsewhere throughout the body. The resultant lesion L1 is symmetrical about electrode E1, as shown in FIG. 7B. The outer electrodes are filled in a solid color to indicate that their switches are closed.

Figure 7C:
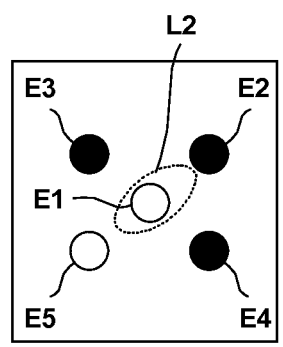
Figure 7D:
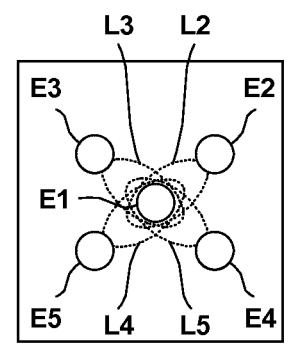

In FIG. 7C switch SW5 to electrode E5 has been opened, indicated by no fill color for this electrode, while the switches to the other outer electrodes remain closed. This results in lesion L2, shaped as shown in FIG. 7C. When this configuration is repeated, opening each other outer electrode in turn while the other three are closed, SW1 to central electrode E1 remaining closed for all cases, a petal-like ablation volume is created as shown in FIG. 7D.

It should be noted that in general the use of various combinations of electrodes as the return path electrode group creates an equivalent, single return path or reference electrode which, although not necessarily symmetric relative to the RF excitation electrode, has a virtual position that can be calculated and thereby allow lesion shape to be predicted. Also, in general, any one of the multiplicity of electrodes can receive the RF excitation voltage, and any of the remaining two or more electrodes can be combined to serve as the return path electrode group.

Creating Very Large, Controlled RF Ablations

Figure 8A:
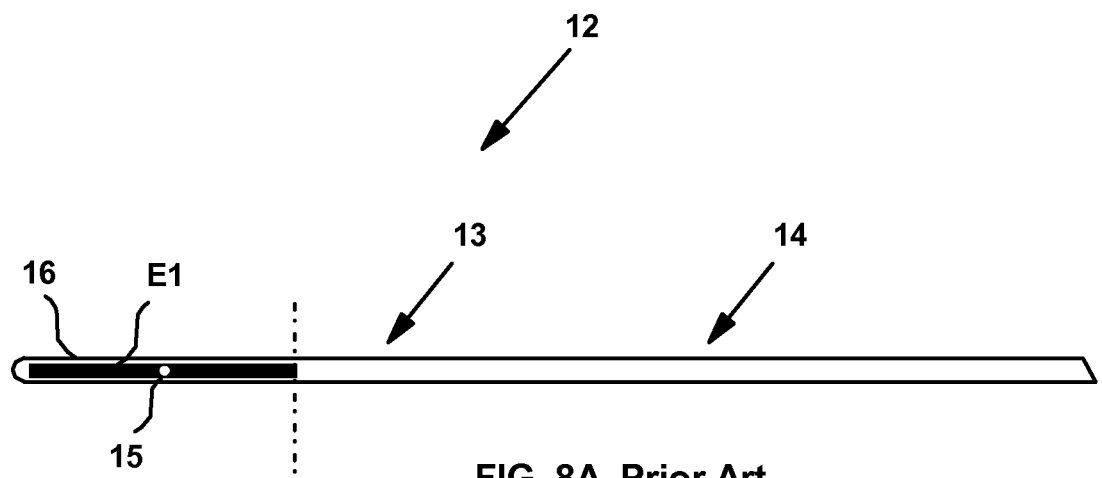
FIGS. 8A and 8B show conventional methods for creating very large RF ablations.

One conventional method for the creation of large or very large RF ablations is illustrated in FIG. 8A which shows an RF probe 12 with a distal end portion 13 and the adjacent portion of its tubular probe body 14, only part of which is shown, and a proximal connector hub, not shown. Distal end portion 13 has a single electrode E1 which contains within in it a temperature sensor 15, usually a thermocouple. The length of electrode E1 typically ranges from 1 to 3 cm, depending on the lesion size required. High tissue temperature, generally in the range of 80 to 90° C., is necessary to produce large lesions, but because of the long length of E1 and consequently its low resistance, high RF currents are required (Energy=Power×Time (the ablation is applied); Power=$I^2$×R where I is current and R is (electrode) resistance). This can result in high current density especially at the electrode tissue interface and cause tissue charring and high tissue interface resistance, limiting the subsequent current and resulting is a much smaller ablation than intended. To avoid this consequence, some RF probes are cooled by the incorporation of a cooling water circulation channel 16 to prevent excessive overheating and charring. This results in a more complex RF probe which also requires a separate pump unit to power the water circulation. It also imposes minimum size limitations on RF probe diameter in order to incorporate the water circulation channel.

The RF probe of FIG. 8A is part of what is termed a monopolar configuration, meaning a single electrode probe, in this instance RF probe 12 and electrode E1 which is connected to the high voltage output of a RF generator, and a large, remote return path electrode which is generally attached to the body surface. Another common conventional electrode configuration is the bipolar RF probe 17 shown in FIG. 8B with its distal end portion containing electrodes E2 and E3 electrically separated by an insulated section 18, and with temperature sensors 19 and 20 incorporated within RF probe 17 close to electrodes E2 and E3 respectively. The RF generator excitation voltage output is connected to E2 and the return path input to E3, or vice versa without consequence. The bipolar electrode configuration limits RF flow current to the local region, but does not decrease the high current and tissue temperature required for large lesions, and therefore the occurrence of tissue charring which prevents optimal ablation volume from being reached. Temperature sensors 19 and 20 provide feedback in an attempt to avoid this occurrence, usually by decreasing current, but this maneuver equally affects both electrodes because all current must flow through each. This makes temperature control less effective because the temperature at each electrode will be different due to a difference in electrode resistances (from variations in electrode surface area and a difference in the composition of surrounding tissue) and therefore feedback must be approximate by using average temperature for best performance or maximum temperature for best safety.

Figure 8B:
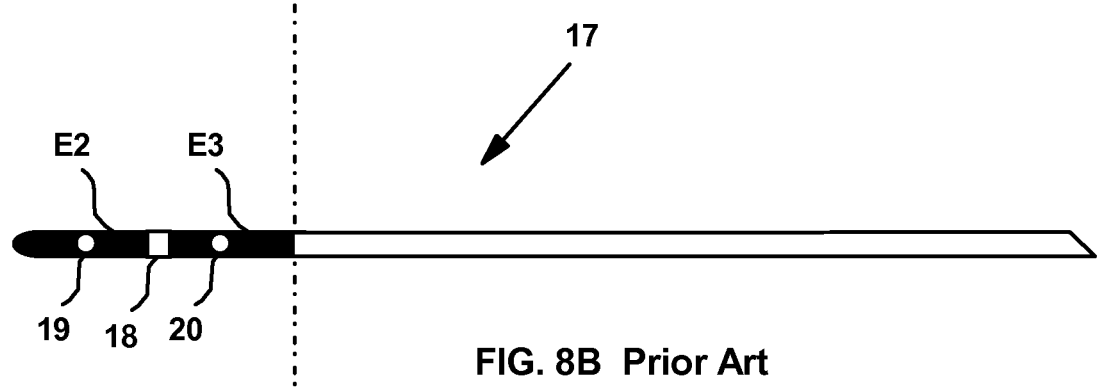
Figure 8C:
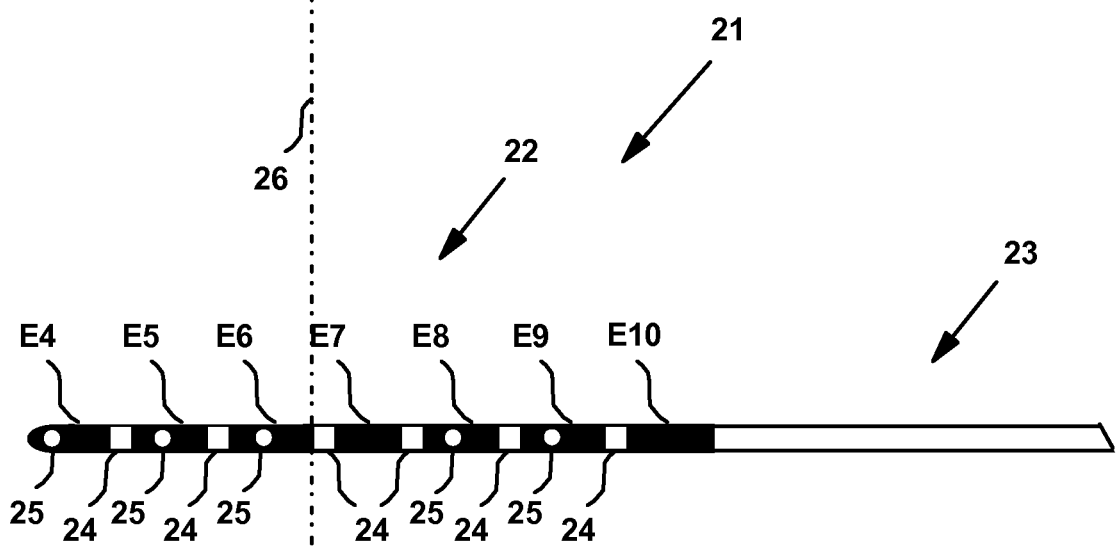
FIG. 8C shows an improved, preferred method of this invention.

The problems associated with conventional monopolar and bipolar electrode configurations of RF probes such as those in FIGS. 8A and 8B are resolved with another preferred embodiment of this invention, an example of which is shown in FIG. 8C. FIG. 8C is a drawing of a multielectrode RF probe 21 with a distal end portion 22 and the adjacent portion of its tubular probe body 23, only part of which is shown, and a proximal connector hub, not shown. RF probe 21 has seven electrodes, E4, E5, E6, E7, E8, E9, and E10, although to achieve the benefits to be described, fewer or more electrodes, and different electrode combinations, could be used. The electrodes are electrically separated by insulated sections 24. There are internal temperature sensors 25 within electrodes E4, E5, E6, E8, and E9, although again to achieve the benefits to be described, fewer or more temperature sensors could be used. Vertical line 26 is used to indicate that the length of the RF probe tip receiving the high output RF voltage is the same in the examples of FIGS. 8A, 8B, and 8C. In the example of FIG. 8C the RF generator of this invention, to be described in the following two sections, connects the high RF voltage first to electrode E4 and the return path to electrodes E7, E8, E9, and E10, thereby establishing a combined low resistance return path electrode relative to electrode E4 and, as has been described previously, much higher current density and heating surrounding electrode E4 which therefore can be controlled precisely and independently of other electrodes by feedback from the temperature sensor within it. Ablations surrounding electrodes E5 and E6 can be similarly created using the same return path electrode group. As previously described, RF applications are incrementally and sequentially distributed over the bipolar electrode sets with electrodes E4, E5 and E6 connected in turn to receive the high RF voltage.

The preceding examples in which electrodes are combined by switches to create a low current density common return path does not necessarily mean that those electrodes must literally be shorted together. Alternatively, the same effect can be accomplished by driving each electrode independently with respect to an unconnected "virtual reference point" and controlling the phase of the excitation voltage or current at each electrode connection.

In the preceding examples in which benefits of various embodiments of multielectrode RF probes are described, the electrodes need not be limited to a single probe. Instead, the electrodes can be distributed advantageously over two or more probes positioned in one or more regions in various alignments to create 2- and 3-dimensional ablation configurations of various sizes and shapes not possible with the use of a single probe. Furthermore, the ability to control the temperature of each electrode independently makes it possible to purposefully vary the temperature throughout a lesion volume, for example decreasing tissue heating in a region near to vital structures.

In addition, the applied energy need not be RF but instead, for example:

(i) conducted heat provided by a small resistive element at the probe's active area excited with either AC or DC current sent along two conductive wires within the probe, or (ii) infrared energy in the infrared optical region radiated from the probe's active area, or coherent or non-coherent infrared radiation coupled down the probe and exiting the probe tip at a controlled angle to be absorbed by and heat the tissue, or (iii) high frequency focused ultrasound.

An RF Generator Based on Multiple Independent RF Switch Control

Figure 9:
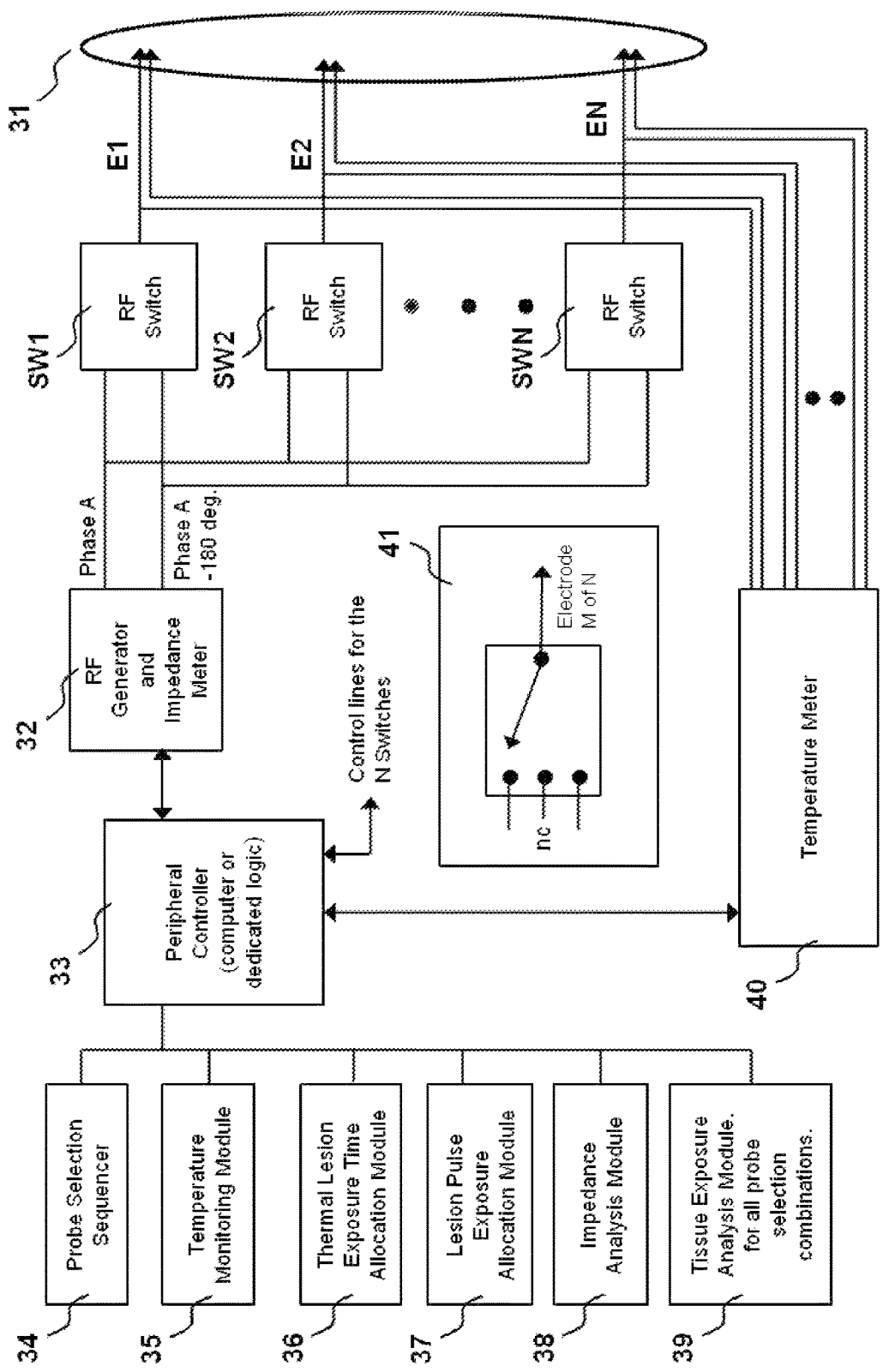
FIG. 9 shows a schematic of an RF generator of this invention based on multiple independent RF switch control.

A preferred embodiment that uses a multiple independent switch based approach is indicated schematically in FIG. 9. It shows RF Generator and Impedance Meter 32 connected to a multiplicity N of electrodes E1, E2, . . . EN in a target tissue region 31 via a corresponding multiplicity of multi-way RF switches SW1, SW2, . . . SWN. The electrodes may be on a single RF probe or more than one RF probe, or in general on other types of probe. The N multi-way RF switches SW1, SW2, . . . SWN are connected to both phases of the RF generator 32 and are used to control the RF excitation of the N electrode patient contacts. The switches are shown in more detail in inset 41 and can be fabricated using naturally isolating mechanical devices such as reed relays or solid state switches with isolated drivers, e.g. FET transistors with photovoltaic isolators and drivers. Or optionally, electrically isolated power supplies and drivers can be used that incorporate various isolating devices based on optical, electric field (capacitive), magnetic (transformer), or RF wave coupling principles.

In addition to a lead wire routed by the switches to the electrodes there can be a second lead wire for a temperature sensor such as a thermocouple within a probe lumen. The use of a single lead wire within a probe lumen in the formation of a thermocouple junction has been described in U.S. patent application Ser. No. 13/188,101, filed Jul. 21, 2011, which is incorporated herein by reference. An alternative approach that provides more wires can be used, for example two lead wires for a thermistor temperature sensor.

RF Generator and Impedance Meter 32 generates at its output terminal the required RF voltage using well established techniques and sends it to selected probe electrodes while measuring the impedance of electrode tissue interfaces that are in effect at various times. It also connects its return path terminal to other electrodes selected for this purpose. The function of Peripheral Controller 33 is to coordinate in a precise manner the timing of the switches and RF generation so that during a time period much shorter than the thermal response time of tissue, the following three events occur for all electrode connection combinations determined by the overall controlling algorithm managed by the Tissue Exposure Analysis Module 39 and the Probe Selection Sequencer 34:

(iv) a controlled amount or RF energy is applied
(v) electrical impedance is measured
(vi) temperature is measured by Temperature Meter 40

Other modules contribute to the calculation as well. The Temperature Monitoring Module 35 acquires the data, performs averaging operations, and provides warning and ramp control as required. The Thermal Lesion Exposure Time Allocation Module 36 and Lesion Pulse Exposure Allocation Module 37 calculate the required RF exposure duration and the Impedance Analysis Module 38 evaluates the impedances as measured when electrode connections are combined and separated and provides information to the control algorithm in the Tissue Exposure Analysis Module 39 about how the ablation is progressing and how RF voltage, power and electrode selection are to be done.

Tissue Exposure Analysis Module 39 generally selects fewer electrode connections in the tissue regions that have not been heated sufficiently when continuous RF current is used or require a high dose of pulsed RF current in order to increase current density in these regions.

Advantageously, the RF generator 32, based on multiple independent RF switch control, uniquely allows the instrument to constantly reconfigure the network topology of the N RF switch connections (SW1 to SWN) to the tissue, i.e. at N tissue nodes, to suit the temperature and heating requirements at any instant. Additionally, a node can be intelligently switched between three states: Current Injection, current return, and disconnection.

An RF Generator Based on Signal Phase and Amplitude Control

Figure 10:
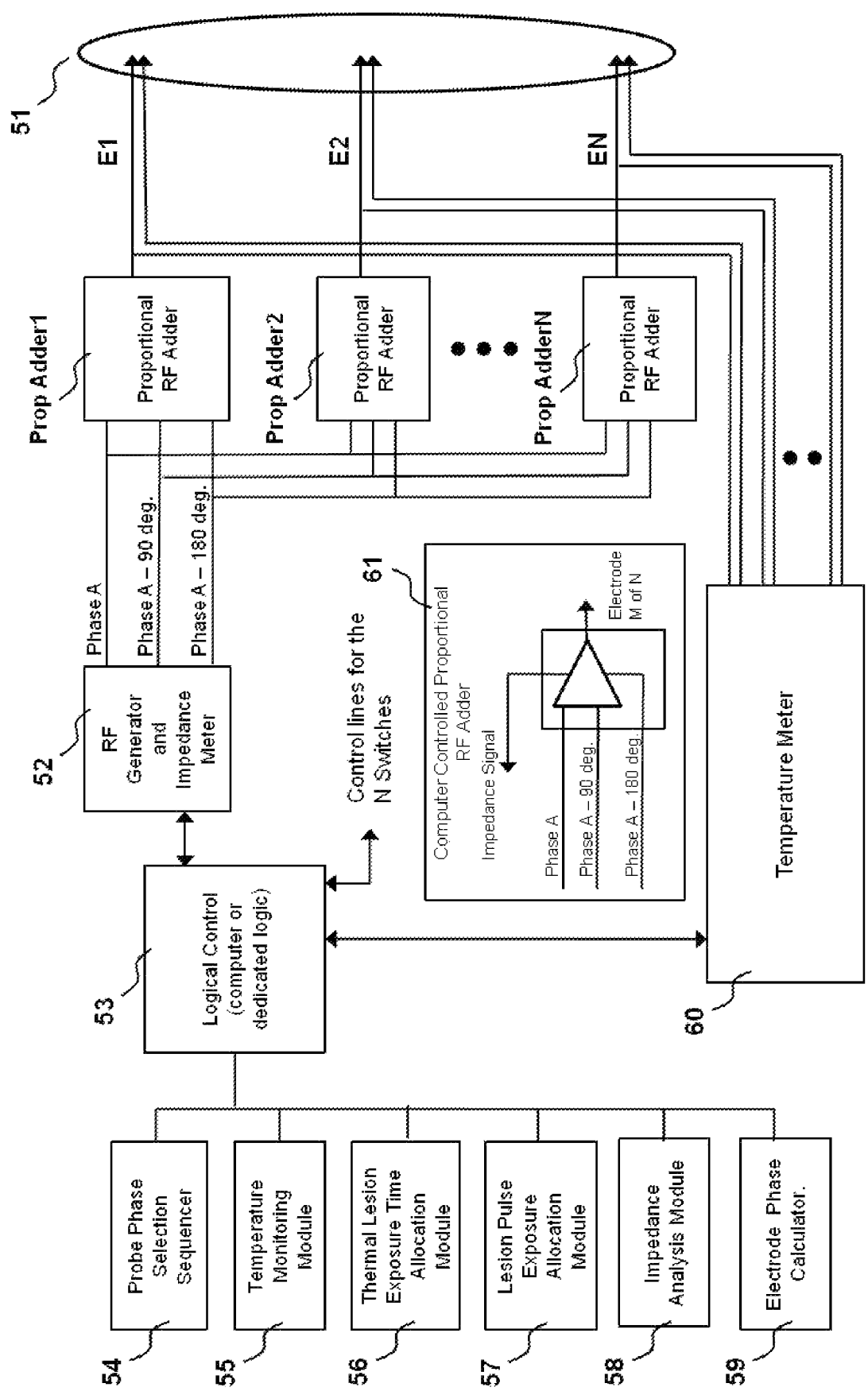
FIG. 10 shows a schematic of another RF generator of this invention based on signal phase and amplitude control.

Another preferred embodiment of an RF generator of this invention that uses a signal phase and amplitude based approach is shown schematically in FIG. 10. RF lesion output from a multi-phase RF Generator and Impedance Meter 52 is routed to a multiplicity N of electrodes E1, E2, . . . EN in a target tissue region 51. The electrodes may be on a single RF probe or more than one RF probe, or in general on other types of probe. In addition to a lead wire for each electrode there can be a second lead wire to a thermocouple temperature sensor serving that electrode, or alternatively, more wires as for example, two lead wires for a thermistor temperature sensor.

The N proportional RF adders, Prop Adder1, Prop Adder2 . . . Prop AdderN, are connected to a controlled variable phase RF output which controls the excitation of each of the N electrodes. The computer controlled proportional RF adder is shown in more detail in insert 61. They can be fabricated with isolated drivers, for example FET transistors. Electrical Isolation can also be established by passing all RF signals through transformers, or with photovoltaic isolators and drivers, or with isolated power supplies and drivers using various isolating devices based on optical, electric field (capacitive), magnetic (transformer), and RF wave coupling principles.

RF Generator and Impedance meter 52 generates the required RF voltage using well established techniques and sends it to selected probe electrodes while measuring the impedance of electrode tissue interfaces that are in effect at various times. The function of Logical Control module 53 is to coordinate the phase and amplitude of the proportional adders and the amplitude of the RF generator's two output phases so that during time periods much shorter than the thermal response time of tissue, the following three events occur for all electrode connection combinations determined by the overall controlling algorithm managed by Electrode Phase Calculator 59 and Probe Phase Selection Sequencer 54:

(i) a controlled amount or RF energy is applied
(ii) electrical impedance is measured
(iii) temperature is measured by Temperature Meter 60

Other modules contribute to the calculation as well. Temperature Monitoring module 55 acquires the data, performs averaging operations, and provides warning and ramp control as required. Thermal Lesion Exposure Time Allocation Module 56 and Lesion Pulse Exposure Allocation Module 57 calculate the required RF exposure time while Impedance Analysis Module 58 evaluates the impedances as measured when electrode connections are combined and separated and provides information to the control algorithm in the Electrode Phase Calculator 59 about the progress of the ablation and how RF voltage, power and electrode probe selection are to be done.

Electrode Phase Calculator 59 generally selects fewer electrode connections in the tissue regions that have not been heated sufficiently or require a high dose of pulsed RF current in order to increase current density in these regions.

The advantage of the phase based approach is that during each incremental step in the RF ablation process there is a something useful that can be done to those electrodes that have not been selected to be strongly connected to either phase of the excitation source. The amplitude and phase of each one can be exactly controlled so it can participate with less current and loads the other excitation electrodes as desired.

Additionally, the RF generator, based on signal phase and amplitude control, is unique because for each tissue node N there are essentially an infinite number of RF signal phase and amplitude combinations that can be applied at it. These combinations can be changed at any point within the lesion cycle thereby modifying as required the temperature and heating requirements at any node at any instant. And, this method allows such control without the need to disconnect any of the RF probe connections.

Statement of General Application

While the applicant's teachings are described in conjunction with various embodiments, it is not intended that the applicant's teachings be limited to such embodiments or to any particular region of the body. On the contrary, the applicant's teachings encompass various alternatives, modifications, and equivalents, and can find diagnostic and therapeutic use in many regions of the body, as will be appreciated by those skilled in the art.

That which is claimed is:

1. A method for forming an ablation, including the steps of:
   providing a first bipolar electrode set having first and second electrode groups, the first electrode group including one or more electrodes and the second electrode group having at least one more electrode than the first electrode group and forms a low impedance return path for RF current;
   wherein each of the one or more electrodes of the first electrode group of the first bipolar electrode set is connected to an excitation voltage;
   wherein the electrodes of the second electrode group of the first bipolar electrode set collectively form the low impedance return path for RF current;
   disposing the first bipolar electrode set within a body;
   providing a second bipolar electrode set having first and second electrode groups, the first electrode group including one or more electrodes and the second electrode group having at least one more electrode than the first electrode group and forms a low impedance return path for RF current;
   wherein each of the one or more electrodes of the first electrode group of the second bipolar electrode set is connected to an excitation voltage;
   wherein the electrodes of the second electrode group of the second bipolar electrode set collectively form the low impedance return path for RF current;
   disposing the second bipolar electrode set within the body;
   applying an energy for a period of time to the first bipolar electrode set to form a first portion of the ablation at the first bipolar electrode set;
   sequentially applying an energy for a period of time to the second bipolar electrode set to form a second portion of the ablation at the second bipolar electrode set;
   repeating the steps of applying the energy to the first bipolar electrode set and then applying the energy to the second bipolar electrode set so as to incrementally form the ablation;
   wherein the number of times of repeating the steps of applying the energy to the first bipolar electrode set and second bipolar electrode set is at least 100 times;
   wherein the period of time for applying the energy to the first bipolar electrode set is in the range of 10 milliseconds to 1500 milliseconds and wherein the period of time for applying the energy to the second bipolar electrode set is in the range of 10 milliseconds to 1500 milliseconds;
   wherein the first bipolar electrode set and the second bipolar electrode set share at least one electrode; and
   wherein the at least one electrode that is shared is disposed within the body.

2. The method according to claim 1, wherein a frequency of repeating the steps of applying the energy to the first bipolar electrode set and second bipolar electrode set is in the range of one per second to 25 per second.

3. The method according to claim 1, wherein the at least one electrode that is shared is within the ablation.

4. The method according to claim 1, further including the step of providing a third bipolar electrode set having first and second electrode groups, the first electrode group including one or more electrodes and the second electrode group including one or more electrodes, and wherein each of the one or more electrodes of the first electrode group of the third bipolar electrode set is connected to an excitation voltage; and
   using said first bipolar electrode set, second bipolar electrode set and third bipolar electrode set in various combinations to create a three-dimensional non-linear ablation volume in order to conform in size and shape to a target volume.

5. The method according to claim 1, further including the step of causing tissue ablation by thermal electrocoagulation during the steps of applying the energy to the first bipolar electrode set and applying the energy to the second bipolar electrode set.

6. The method according to claim 1, wherein each of the electrodes of the first bipolar electrode set and second bipolar electrode set are shared electrodes.

7. The method according to claim 1, further including the step of providing a third bipolar electrode set having first and second electrode groups, the first electrode group including one or more electrodes and the second electrode group including one or more electrodes, and wherein each of the one or more electrodes of the first electrode group of the third bipolar electrode set is connected to an excitation voltage; and
   using said first bipolar electrode set, second bipolar electrode set and third bipolar electrode set in various combinations to create a three-dimensional, long, linear ablation volume in order to conform in size and shape to a target volume.

8. The method according to claim 1, wherein the energy being applied to the first bipolar electrode set is RF energy and the energy being applied to the second bipolar electrode set is RF energy.

9. The method according to claim 1, wherein each electrode of the first bipolar electrode set and the second bipolar set is configured to be independently controlled whereby each electrode is capable of being independently reconfigured as an active electrode or a return electrode.

10. The method according to claim 1, wherein the second electrode group of the first bipolar electrode set creates a reference electrode which has a virtual position.

11. The method according to claim 1, wherein each of the electrodes of the first bipolar electrode set and second bipolar electrode set are shared electrodes.

12. The method according to claim 1, further including the steps of providing a probe, wherein the probe has a central longitudinal axis, wherein each electrode of the first electrode set is disposed on the probe, and wherein at least one electrode of the first bipolar electrode set is offset from the central longitudinal axis of the probe.

13. The method according to claim 1, further including the steps of providing a probe, wherein the probe has a central longitudinal axis, wherein each electrode of the first electrode set is disposed on the probe, and wherein at least one electrode of the first electrode group of the first bipolar electrode set is offset from the central longitudinal axis of the probe.

14. The method according to claim 1, further including the steps of providing a probe, wherein the probe has a central longitudinal axis, wherein each electrode of the first electrode set is disposed on the probe, and wherein at least one electrode of the second electrode group of the first bipolar electrode set is offset from the central longitudinal axis of the probe.

15. The method according to claim 1, further including the steps of providing a probe, wherein the probe has a central longitudinal axis, wherein each electrode of the first electrode set is disposed on the probe, and wherein at least one electrode of the first electrode group of the first bipolar electrode set is offset from the central longitudinal axis of the probe and wherein at least one electrode of the second electrode group of the first bipolar electrode set is offset from the central longitudinal axis of the probe.

\* \* \* \* \*